United States Patent [19]

Oosterwijk et al.

[11] 4,049,726
[45] Sept. 20, 1977

[54] FIRE RETARDANT COMPOUNDS

[75] Inventors: Hendrik Harm Jannes Oosterwijk, Diepenveen; Ulfert Elle Wiersum, Velp; Eduard Pieter Magré, Heelsum; Johannes Hendrinus van Dijk, Ede, all of Netherlands

[73] Assignee: Akzona Incorporated, Asheville, N.C.

[21] Appl. No.: 512,303

[22] Filed: Oct. 4, 1974

[30] Foreign Application Priority Data

Oct. 5, 1973 Netherlands .................... 7313979

[51] Int. Cl.² .................................. C07C 25/18
[52] U.S. Cl. ...................... 260/649 R; 260/649 DP; 260/332.5; 260/45.7 R; 260/45.8 R; 252/8.1
[58] Field of Search ......... 260/649 R, 649 DP, 651 R

[56] References Cited

U.S. PATENT DOCUMENTS

| 2,954,412 | 9/1960 | Wulf et al. ............... 260/651 R |
| 3,200,152 | 8/1965 | Ruppert et al. ........... 260/651 R |
| 3,240,722 | 3/1966 | Orttung et al. ........... 260/651 R |

*Primary Examiner*—D. Horwitz

*Attorney, Agent, or Firm*—Stevens, Davis, Miller & Mosher

[57] ABSTRACT

Novel brominated polydiisopropylarylene compounds which can be used for imparting fire retardance properties to polymers such as polystyrene and polypropylene contain bromine as a substituent on the aliphatic radicals and have the following formula:

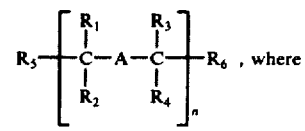

A is a thienylene group or an arylene group such as a substituted or unsubstituted phenylene, biphenylene, napthylene, or anthracylene group, $R_1$ through $R_4$ a methyl group substituted or not with bromine, $R_5$ and $R_6$ a bromine atom or a hydrogen atom, and $n$ a whole number in the range of 2 to 10, the number of bromine atoms per molecule in the aliphatic groups being at least 2 and the total bromine content being not more than 70 per cent by weight.

4 Claims, No Drawings

FIRE RETARDANT COMPOUNDS

The invention relates to a novel group of compounds, namely brominated polydiisopropylarylene compounds having a molecular structure of the following formula:

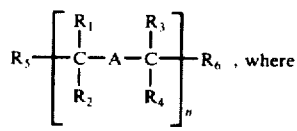, where

A is a thienylene group or an arylene group such as a substituted or unsubstituted phenylene, biphenylene, napthylene, or anthracylene group, $R_1$ through $R_4$ a methyl group substituted or not with bromine, $R_5$ and $R_6$ a bromine atom or a hydrogen atom, and $n$ a whole number in the range of 2 to 10, the number of bromine atoms per molecule in the aliphatic groups being at least 2 and the total bromine content being not more than 70 percent by weight.

The compounds provided by the present invention have been found to form excellent fire retardants in polymer compositions having a basis of polystyrene, copolymers thereof and polypropylene.

It has also been found that this group of compounds is active as a radical initiator and as such may find application in polymerization reactions such as, for instance, the high-temperature polymerization of ethylenically unsaturated compounds such as styrene at temperatures in the range of 100° to 200° C.

It should be added that compounds having as a repeating unit $$\left[ \begin{array}{c} CH_3 \\ | \\ -C- \\ | \\ CH_3 \end{array} \underset{\underset{\underset{}{}}{}}{\overset{Br_m}{\bigcirc}} \begin{array}{c} CH_3 \\ | \\ -C- \\ | \\ CH_3 \end{array} \right], \text{ where}$$

$m$ = not more than 3, have been proposed before as a fire retardant additive for polypropylene in the Belgian Patent Specification No. 737,979.

The essential difference between these compounds and the compounds provided by the invention is that in the case of the Belgian Patent Specification the bromine is exclusively coupled to the aromatic system. Although the percentage bromine in such a compound may be the same as in the compounds provided by the present invention, the presence of an aliphatic bromine compound as a synergist is still required in order to obtain a polymer having sufficient flame retardance.

In this connection mention is made of the book of John W. Lyons: "The Chemistry and Uses of Fire Retardants", Wiley-Interscience, New York (1970), from which it appears (p. 325, last line ff) that styrene brominated in the core is far less effective than, say, vinyl bromide. For this reason he concludes (p. 327) that the use of a brominated aliphatic compound is to be preferred.

As the use of synergistic materials often meet with practical drawbacks, the same applicant of the Belgian Patent Specification had already previously proposed in the German Patent Specification No. 1,258,081 that the ends of the repeating units be coupled to a (poly)butadiene group and/or to a (poly)isoprene group and that these last-mentioned groups be at least partially brominated.

The disadvantage of these compounds, however, is that production of them on an industrial scale is costly and rather complicated in that the coupling of the (poly)butadiene and/or (Poly)isopropene calls for the use of metallic lithium, sodium, potassium, rubidium and/or caesium.

Moreover, with these compounds having a large number of repeating units, there is the risk of the distance between the respective synergistic groups playing a negative role, as a result of which, part of the synergistic effect would be lost again.

It is therefore an object of this invention to provide novel brominated polydiisopropylarylene compounds which can be used to advantage in improving the fire retardance of synthetic polymers. A more specific object of the invention is to provide brominated polydiisopropylarylene compounds which are particularly advantageous for improving the fire retardance of polystyrene and polypropylene. A still further object of the invention is to provide polymers containing the novel brominated polydiisopropylarylene compound and having improved fire retardancy properties.

Applicant has now found that the foregoing disadvantages of the known brominated polydiisopropyl benzene are avoided by the use of the novel compounds provided by the invention. The preparation of the compounds according to the invention has been found possible by starting from the known compound having the formula $$H \left[ \begin{array}{cc} CH_3 & CH_3 \\ | & | \\ -C-A-C- \\ | & | \\ CH_3 & CH_3 \end{array} \right]_n H$$

where $n$ and A have the above-mentioned meaning, and by subjecting this compound to a simple bromination as known to be used for analogous compounds such as cumene.

By carrying out nuclear magnetic resonance measurements (NMR spectra) on the compounds provided by the invention it has been established that no bromine will get into the aromatic systems, but exclusively into the aliphatic groups, the bromine showing a strong preference for the terminal isopropyl groups.

The compounds according to the invention are at least as effective as the known synergistic mixtures in which the bromine is contained in a separate aliphatic compound. Moreover, they have the great advantage that only one substance need be added to the polymer, as a result of which the synergistic effect will always be optimal, even if the added substance is not quite homogeneously distributed in the polymer.

The stability of the compounds provided by the invention is such that under the usual processing conditions there is an insignificant amount of decomposition, if any.

In the above-formulated bromination products of the invention A represents an aromatic groups such as a substituted or non-substituted phenylene, biphenylene, naphthylene, anthracylene group or a thienylene group.

It is preferred that A should be a phenylene group which may, together with the brominated or non-brominated isopropyl groups be included in the structural unit by para or meta substitution. In addition, the phenylene group may contain one or more substituents such as an alkyl group with 1 to 4 carbon atoms such as methyl, ethyl, propyl, butyl, isobutyl, a chlorine atom or a bromine atom and the like. Considering the good effect, the price and the simple processing, however, preference is given to the use of a phenylene group which is coupled to no other substituents than to the isopropyl groups.

Of the compounds provided by the invention those compounds are preferred in which $n = 2$ to 6 and whose bromine content in the aliphatic groups is 20 to 60 percent by weight because these compounds are easiest to process and the range of their bromine content is optimal.

Although the compounds provided by the invention can be incorporated in most polymers at the appropriate processing temperatures practically without being subject to decomposition, it may under some conditions be recommended yet to include substances capable of rendering certain decomposition products such as HBr harmless. In this connection mention is made of organotin compounds such as dibutyltinbis(octylthiopropionate), lead compounds such as lead sulphate and lead oxide, metal soaps such as cadmium stearate and basic lead stearate, organic phosphites such as triisodecyl phosphite and triphenyl phosphite, and epoxy oils such as epoxidized soybean oil. This enumeration is, of course, not meant to be limitative, so that also other substances may be used to advantage.

The bromine content of the polymeric end product should generally be at least 0.1% by weight and not more than 5% by weight. It is preferred to use a bromine content in the range of 0.5 to 2 percent by weight.

As a rule, the flame retardant bromine compound together with one or more of the other additives should be present in an amount not higher than 5% by weight of the polymer. Although it is possible to use larger amounts, they often have a negative influence on the properties of the polymer.

The compounds provided by the invention may be incorporated to advantage in many types of polymers. Particularly favorable results are obtained when they are contained in polypropylene and polystyrene polymers or copolymers.

By polymer compositions having a basis of polystyrene are to be understood here both polystyrene and copolymers thereof, the latter containing at least 50 percent by weight of the styrene monomer. Examples of other monomers that may be incorporated in the copolymers according to the invention are: α-methylstyrene, acrylonitrile, methacrylonitrile, esters of acrylic acid or methacrylic acid with alcohols having 1 to 8 carbon atoms, esters of fumaric acid with alcohols having 1 to 8 carbon atoms, vinyl pyridine, N-vinyl compounds such as N-vinyl carbazole, butadiene or also small quantities, for instance 0.001 to 1 and preferably 0.01 to 0.1 percent by weight of divinyl benzene.

By polymer compositions having a basis of polypropylene are to be understood here both polypropylene and copolymers thereof, the latter containing at least 50 percent by weight of the propylene monomer.

The compounds according to the invention also may find application in impact resistant polystyrene composed on a basis of styrene and, if desired, other monomers and finely divided rubber-like polymers.

The compounds provided by the invention used in thermoplastic self-extinguishing molded articles may, of course, also be made to contain other substances such as fillers, dyes, pigments, release agents, plasticizers, antistats, aging means, stabilizers or foaming compounds.

The novel compounds provided by the invention may be incorporated in the thermoplastic molded articles by mixing the bromine compounds with the polymer and, if desired, with other components. This may be done on the roll, in the extruder or in a kneading machine. Or, they may be added to the monomers prior to polymerization. Alternatively, for instance, in the manufacture of cast film, the compounds according to the invention may be added to a solution of the synthetic material, followed by evaporation of the solvent. By adding the compounds prior to polymerizaton a particularly homogeneous distribution is obtained. In the case of polystyrene it has been found that probably as a result of the presence of aromatic groups the compounds according to the invention are more satisfactorially held in the polymer than when use is made of the known fire retardant aliphatic bromine compounds. This last-mentioned advantage is of great importance not only for prolonged retention of self-extinguishing properties, but also for physiological reasons.

The invention will now be further described in the following examples which, of course, must not be considered in any way to limit the scope of the present invention.

The flame retardance in the following examples was determined by means of the Limiting Oxygen Index (LOI), measured in conformity with ASTM D 2863-70, unless indicated otherwise.

The higher the LOI value, the higher will be the flame retardance of the polymer composition.

EXAMPLE I

Preparation of brominated polydiisopropyl benzene

Into a three-necked flask provided with a stirrer, a thermometer, a dropping funnel and a reflux condenser, were charged 100 g. poly-m-diisopropyl benzene. To this substance were added, in the presence of UV light, 108 g. bromine over a period of 3 hours at 85° C. After the mixture had been stirred for 4 hours at 85° C., it was cooled and brought into 200 ml. benzene and washed acid-free with a 10% by weight solution of NaHCO₃. The product was dried on magnesium sulphate, after which the benzene was evaporated off. The yield was 150.3 g., the bromine content being 33.3% by weight.

By nuclear magnetic resonance measurement (NMR) it could be established that the bromine was exclusively contained in the aliphatic groups. Upon further analysis the product was found to be composed as follows:

60% by weight dimer
21% by weight trimer
19% by weight tetramer + higher oligomers.

EXAMPLE II

Preparation of brominated polydiisopropyl benzene

Into the three-necked flask of Example 1 were charged 98 g. poly-m-diisopropyl benzene together with 100 ml. carbon tetrachloride and 1 ml. pyridine. After the mixture had been heated to 70° C., 2 ml. water and a few crystals of iodine were added. Subsequently, 250 g., bromine were added dropwise over a period of 7 hours, after which the reaction mixture was stirred for three more hours at 78° C.

The reacton mixture was concentrated by evaporation under reduced pressure (2 mm.Hg) at about 50° C., as a result of which a viscous liquid was obtained, from which after dissolving in petroleum either and cooling down 171.1g solid matter could be isolated.

The bromine content of the resulting product was 46.7% by weight.

Here, too, it was found by nuclear magnetic resonance measurement that the bromine was exclusively contained in the aliphatic groups.

The composition of the product was as follows:
60% by weight dimer
21% by weight trimer
19% by weight higher polymer

EXAMPLE III

Fire retardant polystyrene

An amount of polystyrene beads (marketed under the trade name Polystyrol 145D Glaskar 012 by Badische Anilin und Sodafabrik) together with successively 1, 3 and 5% by weight of the brominated poly-diisopropyl benzene of Example I was dissolved in dichloromethane (1 part of solid substance in 5 parts of solvent). After the mixture had been poured onto a glass plate and air dried, a film was obtained which was dried for 2 more hours in vacuo at 100° C. After the film had been cooled, it was ground into a coarse powder in a cross beater mill.

The powder obtained was molded into rectangular test specimens measuring 150 × 6.5 × 3 mm. at a temperature of 150° C. and over a period of about 1½ minutes.

Of the best specimens thus obtained the values of the Limiting Oxygen Index (LOI) were determined. The results are shown in Table 1.

TABLE 1

| Run | % by weight of brominated poly-m-diisopropyl benzene | LOI-value |
|---|---|---|
| 1 | 0 | 18.3 |
| 2 | 1 | 25.8 |
| 3 | 3 | 27.8 |
| 4 | 5 | 29.7 |

EXAMPLE IV

Fire retardant polystyrene

The preparation of fire retardant polystyrene was carried out in the same way as in Example III, except that this time use was made of the brominated poly-m-diisopropyl benzene of Example II, which has a bromine content of 46.7% by weight.

The results of these experiments are listed in the following table.

TABLE 2

| Run | % by weight of brominated poly-m-diisopropyl benzene | LOI-value |
|---|---|---|
| 1 | 1 | 26.3 |
| 2 | 3 | 28.9 |
| 3 | 5 | 31.6 |

EXAMPLE V

Fire retardant polystyrene

Forty nine parts by weight of polystyrene powder obtained by grinding polystyrene beads (marketed under the trade name Polystyrol 145D Glaskar 012 by Badische Anilin und Sodafabrik) were intimately mixed with one part by weight of the powdered brominated poly-diisopropyl benzene of Example I. The resulting mixture was extruded by means of a laboratory extruder provided with a type of screw normally used for the processing of polystyrene and having a diameter of 19 mm., a length of 380 mm. and a compression ratio of 2.5:1.

Use was made of such an extruder head that the extrudate was obtained in the form of an endless bar having a practically rectangular cross-section of 6.5 × 3 mm.

The extrusion temperature was 180° C.; the rotational speed of the screw was so set that the average residence time of the polystyrene mixture in the heated parts of the extruder was about 1 minute.

The extrudate obtained was cut into straight specimens 150 mm. long. An LOI value of 26.7 was found.

EXAMPLE VI

Fire retardant polystyrene

The preparation of fire retardant polystyrene was done with the use here of poly-p-diisopropyl benzene brominated entirely in accordance with the procedure of Example I used for poly-m-diisopropyl benzene.

The polymer contained 83% by weight of dimer and 17% by weight of higher oligomers. The bromine content was 29.1% by weight. Entirely on the analogy of Example III polystyrene mixtures containing 1, 3 and 5 percent by weight of this brominated oligomer mixture were composed. Also the preparation of the test specimens was carried out entirely in accordance with the procedure described in Example III. The results of the LOI tests are given in the following table.

TABLE 3

| Run | % by weight of brominated poly-p-diisopropyl benzene | LOI-value |
|---|---|---|
| 1 | 1 | 25.3 |
| 2 | 3 | 25.8 |
| 3 | 5 | 26.3 |

EXAMPLE VII

Fire retardant polystyrenes

An amount of polystyrene beads (high-impact polystyrene, code no. 87-88-1 of the Badische Anilin und Sodafabrik) was dissolved in dichloromethane in the same way as described in Example III.

To separate fractions thereof were added brominated polydiisopropyl benzene in amounts of up to 1.04, 3.12 and 5.20% by weight. The bromine content of the polydiisopropyl benzene was 53.6% by weight. The best specimens were prepared in the same way as indicated in Example III, except that they were molded at a temperature of 140° C. for about 1 minute.

The results of the LOI test are listed in the table below.

TABLE 4

| Run | % by weight of brominated polydiisopropyl benzene | LOI-value |
|---|---|---|
| 1 | 0 | 18.4 |
| 2 | 1.04 | 23.3 |
| 3 | 3.12 | 24.9 |
| 4 | 5.20 | 26.2 |

EXAMPLE VIII

Fire retardant styrene-acrylonitrile copolymer

An amount of this copolymer marketed under the trade name Luran 368 R by the Badische Anilin und Sodafabrik together with brominated polydiisopropyl benzene (bromine content 53.6% by weight) was dissolved in dichloromethane and divided into a few fractions which, while in the dry state, contained 1.04, 3.12 and 5.20% by weight of brominated polydiisopropyl benzene, respectively. The test specimens were prepared entirely in accordance with the way indicated in Example III, except that they were molded at about 150° C. for about 1 minute.

The results of the LOI test are listed in the table below.

TABLE 5

| Run | % by weight brominated polydiisopropyl benzene | LOI-value |
|---|---|---|
| 1 | 0 | 19.0 |
| 2 | 1.04 | 22.0 |
| 3 | 3.12 | 29.0 |
| 4 | 5.20 | 30.9 |

EXAMPLE IX

Fire retardant polypropylene

Polypropylene powder made from Propathene D 454 A marketed by Imperial Chemical Industries was divided into a number of fractions which were treated with an approximately 10% by weight solution of brominated poly-m-diisopropyl benzene in dichloromethane. After the solvent had been removed by evaporation, the fractions, which contained 1.3 and 5% by weight of brominated poly-m-diisopropyl benzene, respectively, were molded into bars at 180° C. for about 1 minute in the same way as indicated in Example III.

The results of the LOI tests are given in the following table.

TABLE 6

| Run | % by weight of brominated poly-m-diisopropyl benzene | LOI-value |
|---|---|---|
| 1 | 0 | 17.2 |
| 2 | 1 | 24.6 |
| 3 | 3 | 25.6 |
| 4 | 5 | 26.7 |

Although the invention is described in detail for the purpose of illustration it is to be understood that such detail is solely for that purpose and that variations can be made therein by those skilled in the art without departing from the spirit and scope of the invention except as it may be limited by the claims.

What is claimed is:

1. A brominated polydiisopropylarylene compound having a molecular structure of the following formula

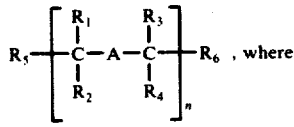, where

A is an arylene group, $R_1$, $R_2$, $R_3$ and $R_4$ are methyl groups or methyl groups substituted with bromine, $R_5$ and $R_6$ are bromine or hydrogen, and $n$ a whole number of 2 to 10, the number of bromine atoms per molecule in the aliphatic groups being at least 2 and the total bromine content being not more than 70 percent by weight.

2. Brominated polydiisopropylarylene according to claim 1, wherein $n = 2$ to 6 and the bromine content of the aliphatic groups is in the range of 20 to 60 percent by weight.

3. A new product having the formula

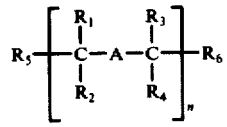

wherein $R_1$, $R_2$, $R_3$ and $R_4$ are methyl, bromomethyl, dibromomethyl or tribromomethyl and are the same or different from each other, $R_5$ and $R_6$ are bromine or hydrogen and are the same or different from each other, $n$ is a whole number of 2 to 10, A is phenylene, biphenylene, naphthylene, or anthracylene, unsubstituted or substituted with an alkyl group having 1 to 4 carbon atoms, bromine or chlorine, the number of bromine atoms per molecule on the aliphatic groups being at least 2 and the total bromine content being not more than 70 percent by weight of the product.

4. The product of claim 3 wherein $R_1$, $R_2$, $R_3$ and $R_4$ are methyl, $R_5$ and $R_6$ are bromine, A is phenylene and $n$ is 2.